(12) United States Patent
Grosjacques et al.

(10) Patent No.: US 10,667,999 B2
(45) Date of Patent: *Jun. 2, 2020

(54) TINTING SHAMPOOS

(71) Applicant: Henkel AG & Co. KGaA, Duesseldorf (DE)

(72) Inventors: Camille Grosjacques, Hamburg (DE); Yvonne Lissner, Hamburg (DE); Susanne Bietz, Elmshorn (DE); Katharina Krause, Hamburg (DE); Daniel Eisebitt, Pinneberg (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/226,304

(22) Filed: Dec. 19, 2018

(65) Prior Publication Data

US 2019/0183769 A1 Jun. 20, 2019

(30) Foreign Application Priority Data

Dec. 20, 2017 (DE) .................. 10 2017 223 420

(51) Int. Cl.
| | | |
|---|---|---|
| *A61Q 5/10* | (2006.01) | |
| *A61K 8/60* | (2006.01) | |
| *A61K 8/41* | (2006.01) | |
| *A61K 8/19* | (2006.01) | |
| *A61Q 5/02* | (2006.01) | |
| *A61Q 5/06* | (2006.01) | |
| *A61K 8/44* | (2006.01) | |

(52) U.S. Cl.
CPC .............. *A61K 8/604* (2013.01); *A61K 8/19* (2013.01); *A61K 8/416* (2013.01); *A61K 8/442* (2013.01); *A61Q 5/02* (2013.01); *A61Q 5/065* (2013.01); *A61K 2800/432* (2013.01); *A61K 2800/48* (2013.01)

(58) Field of Classification Search
CPC .... A61Q 5/065; A61Q 5/02; A61K 2800/432; A61K 2800/43; A61K 8/46; A61K 8/604; A61K 2800/5424; A61K 8/602; A61K 8/45; A61K 2800/5428; A61K 47/14; A61K 8/4993; A61K 47/186; A61K 8/442

See application file for complete search history.

(56) References Cited

U.S. PATENT DOCUMENTS

| | | | |
|---|---|---|---|
| 7,674,299 B2 | 3/2010 | Huet et al. | |
| 8,858,652 B2 | 10/2014 | Witte et al. | |
| 2008/0282481 A1* | 11/2008 | De Boni | A61K 8/817 |
| | | | 8/405 |
| 2014/0137342 A1* | 5/2014 | Guerin | A61K 8/4926 |
| | | | 8/405 |

FOREIGN PATENT DOCUMENTS

| | | |
|---|---|---|
| DE | 10114979 A1 | 10/2002 |
| EP | 1504749 A1 | 2/2005 |
| EP | 1935455 A1 | 6/2008 |
| EP | 2184051 A1 | 5/2010 |
| EP | 2196186 A1 | 6/2010 |
| EP | 2277500 A1 | 1/2011 |
| WO | 2013041485 A2 | 3/2013 |
| WO | 2013082413 A1 | 6/2013 |
| WO | 2014149019 A1 | 9/2014 |
| WO | 2016040158 A1 | 3/2016 |

* cited by examiner

*Primary Examiner* — Eisa B Elhilo
(74) *Attorney, Agent, or Firm* — Lorenz & Kopf, LLP

(57) ABSTRACT

The disclosure relates to an agent for the dyeing of keratinic fibers, in particular human hair, containing in a cosmetic carrier
(a) at least one direct-acting dye,
(b) at least one amphoteric surfactant, in particular at least one alkyl betaine, and
(c) at least one alkyl polyglycoside, in particular at least one alkyl polyglucoside,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c). The disclosure also relates to the use of the agent for the dyeing of keratinic fibers, and to a method in which the agent for the dyeing is applied to the keratinic fibers.

18 Claims, No Drawings

TINTING SHAMPOOS

CROSS-REFERENCE TO RELATED APPLICATION

This application claims priority to German Patent Application No. 10 2017 223 420.2, filed Dec. 20, 2017, which is incorporated herein by reference in its entirety.

TECHNICAL FIELD

The present disclosure is in the field of cosmetics and relates to agents for the dyeing (hereinafter also referred to as a colorant) of keratinic fibers, in particular human hair, which agents contain in a cosmetic carrier at least one direct-acting dye and a combination of at least one amphoteric surfactant and at least one alkyl polyglycoside. These colorants are particularly suitable for:
  Increasing the chromaticity of the dyes on the keratinic fiber and/or
  Increasing the color lift of the dyes on the keratinic fiber and/or
  Increasing the color intensity of the dyes on the keratinic fiber.

A second subject of the present disclosure is a method of coloring keratinic fibers, in which a colorant containing a combination of at least one amphoteric surfactant and at least one alkyl polyglycoside is used as the non-ionic surfactant.

A third subject of the present disclosure is the use of the agent of the present disclosure for coloring keratinic fiber which agent uses a colorant containing a combination of at least one amphoteric surfactant and at least one alkyl polyglycoside.

BACKGROUND

The change in shape and color of keratinic fibers, in particular hair, represents an important sector of modern cosmetics. As a result, the appearance of the hair can be adapted to both current fashion trends and the individual wishes of the individual person. The person skilled in the art knows various dyeing systems for changing hair color, depending on the requirements of the coloring. Oxidation colorants are usually used for permanent, intense colorings with good fastness properties and good gray coverage. Such colorants usually contain oxidation dye precursors, so-called developer components and coupler components, which, under the influence of oxidizing agents, for example, hydrogen peroxide, form the actual dyes with each other. Oxidation colorants are exemplified by excellent, long-lasting coloring results but are also associated with some degree of hair damage.

If the user wants to reduce hair damage or change hair color only temporarily, he can resort to colorants that are based on direct-acting dyes. In this case, already formed dyes diffuse from the colorant into the hair fiber. In comparison with oxidative hair dyeing, the colorings obtained with direct-acting dyes have lower durability and faster leachability. Also, gray coverage, which can be obtained with direct-acting dyes, is usually in need of improvement. Of advantage, however, is the lower hair damage of the coloring with direct-acting dyes.

Depending on the desired color result, the person skilled in the art uses direct-acting dyes of different classes of dyes. The direct-acting dyes known from the prior art include, for example, the class of nitro dyes, the anthraquinone dyes, the azo dyes, the triarylmethane dyes or the methine dyes. All of these classes of dyes should meet a specific requirement profile for use in the cosmetics sector. Thus, direct-acting dyes should provide an intense dyeing result and have the best possible fastness properties. The color result obtained with direct-acting dyes should be influenced as little as possible by to environmental influences, that is, the dyes should have, for example, a good wash fastness, light fastness and friction fastness. Also, chemical influences that the keratinic fibers may be exposed to after the dyeing process (such as perms) should change the color result as little as possible.

Direct-acting dyes can be subdivided into anionic, cationic and non-ionic direct-acting dyes. In cosmetic compositions, these interact in different ways with the other constituents of the compositions. Surface-active active ingredients contained here, such as surfactants or emulsifiers, have a significant influence. These are intended to relieve the keratinic fibers from impurities in the cosmetic compositions and/or to emulsify constituents of the composition itself. However, in this case, depending on the choice of the surface-active substance, it can also lead to interactions between these and the direct-acting dyes, whereby the dyeing result is sometimes significantly deteriorated compared to agents that do not contain surface-active substances.

Surfactants or emulsifiers are amphiphilic (bifunctional) compounds which include at least one hydrophobic and at least one hydrophilic molecular component. The hydrophobic radical is usually a hydrocarbon chain. The hydrophilic radical can have a negative charge, a positive charge, a negative and a positive charge, or no charge, depending on the type of the surfactant.

For anionic surfactants, the hydrophilic component comprises at least one negatively charged hydrophilic head group. Anionic surfactants contain only negative charges.

Cationic surfactants are understood to mean surfactants, that is, surface-active substances, each having one or more positive charges. Cationic surfactants contain only positive charges.

In the hydrophilic molecular component, zwitterionic (amphoteric) surfactants comprise at least one negatively charged and at least one positively charged group. These are spatially separated from each other and lie next to each other, wherein the surfactant is electrically neutral as a whole.

In addition, there are non-ionic (non-ionogenic) surfactants which are exemplified by the absence of electrical charges in the molecules.

It has long been known to the person skilled in the art that many surfactants can significantly degrade the color lift of direct-acting dyes on keratinic fibers. Not all types of surfactants are compatible with all types of direct-acting dyes. The color lift of direct-acting dyes depends to a significant extent on the nature of the surfactants and the nature of the dyes. Anionic surfactants in particular negatively influence the color lift of non-ionic and cationic dyes, but also of anionic dyes. In contrast, cationic surfactants in particular have a negative influence on the color lift of non-ionic and anionic dyes, but also of cationic dyes.

To circumvent these problems, so far, only compositions in which the dye and the surfactant are precisely matched are usually used. It is therefore not possible to use any desired dye with each surfactant or to combine a plurality of dyes with one another in order to achieve the desired shade.

Accordingly, such various compositions are described in the prior art. EP 1 935 455 A1 discloses a composition comprising a direct-acting dye in combination with at least one bioheteropolysaccharide, at least one cationic surfactant and at least one amphoteric surfactant.

WO 2013/041485 A2 describes a composition comprising at least one dye, for example a direct-acting dye, at least one fatty body in the form of a long-chain dialkyl carbonate or dialkenyl carbonate, at least one non-ionic surfactant and at least one cationic and/or amphoteric polymer. Cleaning compositions having different combinations of surfactants are described, for example, in WO 2016/040158 A1, WO 2013/082413 A1 and WO 2014/149019 A1. None of these compositions is especially suitable for the improved color application of direct-acting dyes.

Conventional surfactant-containing colorants having direct-acting dyes (tinting shampoos) are usually optimized either to the best possible dyeing properties or to the best possible cleaning properties or the best possible foam formation. The choice of direct-acting dyes and surfactants that can be combined with each other is limited, so that the flexibility of the possible dye combinations of direct-acting dyes is limited.

The present disclosure therefore had the object of providing a surfactant-containing colorant based on direct-acting dyes, which colorant is compatible with a wide variety of direct-acting dyes and ensures a good color lift.

In addition, the agent should allow a possible large variety of colors, chromaticity and color intensity.

Finally, the agent should also have good cleaning action and good foaming properties and be easily applicable.

BRIEF SUMMARY

Agents and methods for dyeing of keratinic fibers are provided herein. In an embodiment, an agent for dyeing of keratinic fibers includes, in a cosmetic carrier, (a) at least one direct-acting dye, (b) at least one amphoteric surfactant, and (c) at least one alkyl polyglycoside. The total amount of amphoteric surfactant (b) in the agent, based on the weight of the agent, is less than the total amount of alkyl polyglycoside (c) or equal to the total amount of alkyl polyglycoside (c).

In another embodiment, an agent for dyeing of keratinic fibers includes, in a cosmetic carrier, (a) at least one direct-acting dye, (b) at least one amphoteric surfactant, and (c) at least one alkyl polyglycoside. The at least one direct-acting dye (a) is present in a total amount from about 0.001 to about 7% by weight, based on the weight of the agent. The at least one amphoteric surfactant (b) is present in a total amount of from about 0.5 to about 15.0% by weight, based on the weight of the agent. The at least one alkyl polyglycoside (c) is present in a total amount of from about 0.5 to about 15.0% by weight. The total amount of amphoteric surfactant (b) in the agent, based on the weight of the agent, is less than the total amount of alkyl polyglycoside (c) or equal to the total amount of alkyl polyglycoside (c). The total content of amphoteric surfactant (b) and alkyl polyglycoside (c) together is from about 1.0 to about 25.0% by weight, based on the total weight of the agent.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description Surprisingly, it has now been found that a plurality of different direct-acting dyes in a surfactant-containing, cosmetic composition, in particular a shampoo (tinting shampoo) can be used with improved coloring individually or in combination with each other when the surfactant-containing cosmetic composition comprises at least one direct-acting dye, in combination with at least one amphoteric surfactant and at least one alkyl polyglycoside.

A particularly good color lift could be achieved when the weight-related total amount of amphoteric surfactant is less than or equal to the weight-related total amount of alkyl polyglycoside. Further improvements in color lift could be observed when the surfactant-containing formulations were prepared using sodium chloride-free surfactant preparations.

A first subject of the present disclosure is an agent for the dyeing of keratinic fibers, in particular human hair, containing in a cosmetic carrier
(a) at least one direct-acting dye,
(b) at least one amphoteric surfactant, in particular at least one alkyl betaine, and
(c) at least one alkyl polyglycoside,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c).

Keratinic fibers are understood to mean furs, wool, feathers and in particular human hair. Although the agents are primarily suitable for dyeing keratin fibers, in principle, there is nothing to prevent their use in other areas as well. The term "agent for the dyeing" of keratin fibers is understood to mean colorants which dye the keratin fibers on the basis of direct-acting dyes. Characteristic of the agent as contemplated herein is its content of the essential ingredients (b) and (c). It has been found that particularly advantageous agents can be obtained when the weight-related total amount of amphoteric surfactant in the agent, based on the weight of the agent, is less than or equal to the weight-related total amount of alkyl polyglycoside.

The agent as contemplated herein contains at least one direct-acting dye (a) as a first essential ingredient.

The direct-acting dye(s) (a) is or are preferably present in a total amount from about 0.001 to about 7% by weight, preferably from about 0.01 to about 5.5% by weight, more preferably from about 0.08 to about 3.4% by weight, more preferably from about 0.1 to about 2% by weight, more preferably from about 0.3 to about 1.5% by weight and particularly preferably from about 0.6 to about 1% by weight, each based on the weight of the colorant.

Direct-acting dyes (a) can be subdivided into anionic, cationic and non-ionic direct-acting dyes. The direct-acting dyes are usually selected from the nitrophenylenediamines, the nitroaminophenols, the azo dyes, the anthraquinones, the triarylmethane dyes or the indophenols and their physiologically compatible salts.

One skilled in the art refers to dyes that carry only anionic charges as acid dyes. The terms anionic dye and acid dye are therefore used synonymously in the context of this disclosure. Anionic dyes or acid dyes are understood to mean direct-acting dyes which have at least one carboxylic acid group (—COOH) and/or at least one sulfonic acid group (—SO3H). Depending on the pH value, the protonated forms (—COOH, —SO3H) of the carboxylic acid or sulfonic acid groups are present in equilibrium with their deprotonated forms (—COO—, —SO3-). As the pH value decreases, the proportion of protonated forms increases. If direct-acting dyes are used in the form of their salts, the carboxylic acid groups or sulfonic acid groups are present in deprotonated form and are neutralized to maintain electroneutrality with appropriate stoichiometric equivalents of cations (such as Na cation or K cations). An anionic dye does not carry cationic charges.

As suitable acid dyes, for example, one or more compounds can be selected from the following group: Acid Yellow 1 (D&C Yellow 7, Citronin A, Ext. D&C Yellow No. 7, Japan Yellow 403, CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (CI 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; no sodium salt; Brown No. 201; RESORCIN BROWN; ACID ORANGE 24; Japan Brown 201; D & C Brown No. 1), Acid Red 14 (CI14720), Acid Red 18 (E124, Red 18; CI 16255), Acid Red 27 (E 123, CI 16185, C-Rot 46, Echtrot D, FD&C Red Nr. 2, Food Red 9, Naphtholrot S), Acid Red 33 (Red 33, Fuchsia Red, D&C Red 33, CI 17200), Acid Red 35 (CI CI18065), Acid Red 51 (CI 45430, Pyrosin B, Tetraiodofluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI CI 27290), Acid Red 87 (Eosin, CI 45380), Acid Red 92 (D&C Red; Red 104; AKA231; RED 28; SUREDYE; 11969 Red; PHLOXINE; CI 45405; CI 45410; EOSINE B); Acid Red 95 (CI 45425, Erythrosine, Simacid Erythrosine Y), Acid Red 184 (CI 15685), Acid Red 195; Pigment Red 57:1 (E180; D & CRED7; CI 15850; Rubine 4BN; CI 15850:1; PIGMENT RED 57; Litholrubine BK; LITHOLRUBINE RB; LITHOLRUBINE BCA; Lithol Rubine B); Acid Violet 43 (Jarocol Violet 43, Ext. D&C Violet no 2, CI 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucine A, CI 42090, CI Food Blue 2), Acid Blue 62 (CI 62045), Acid Blue 74 (E 132, CI 73015), Acid Blue 80 (CI 61585), Acid Green 3 (CI 42085, Foodgreen1), Acid Green 5 (CI 42095), Acid Green 9 (CI 42100), Acid Green 22 (CI 42170), Acid Green 25 (CI 61570, Japan Green 201, D&C Green No. 5), Acid Green 50 (Brilliant Acid Green BS, CI 44090, Acid Brilliant Green BS, E 142), Acid Black 1 (Black no 401, Naphthalene Black 10B, Amido Black 10B, CI 20470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Brown 1, bromophenol blue and/or tetrabromophenol blue.

In a further particularly preferred embodiment, an agent as contemplated herein contains (a) at least one anionic direct-acting dye selected from the group including Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and D&C Brown 1.

Most preferably, an agent as contemplated herein comprises at least one anionic direct-acting dye (a) from the group Acid Orange 7, Acid Red 33, Acid Red 92; Acid Violet 43, Acid Blue 9, Acid Blue 62 and Acid Black 1.

The anionic direct-acting dye(s) (a) are preferably present in a total amount from about 0.001 to about 7% by weight, preferably from about 0.01 to about 5.5% by weight, more preferably from about 0.1 to about 3.4% by weight and particularly preferably from about 0.3 to about 2% by weight, each based on the weight of the colorant.

Further preferred colorants as contemplated herein contain at least one cationic direct-acting dye as direct-acting dye (a). Dyes that carry only cationic charges are commonly referred to as basic dyes.

Examples of suitable basic (cationic) dyes to be mentioned are: Basic Blue 6 (CI-No. 51,175), Basic Blue 7 (CI-No. 42,595) Basic Blue 9 (CI-No. 52,015), Basic Blue 26 (CI-No. 44,045), Basic Blue 41 (CI-No. 11,154), Basic Blue 99 (CI-No. 56,059), HC Blue 15, HC Blue 16 (Blue Quat Bromide), Cationic Blue 347, Basic Brown 4 (CI-No. 21,010), Basic Brown 16 (CI-No. 12,250), Basic Brown 17 (CI-No. 12,251), Natural Brown 7 (CI-No. 75,500), Basic Green 1 (CI-No. 42,040), Basic Red 2 (CI-No. 50,240), Basic Red 22 (CI-No. 11,055), Basic Red 51, Basic Red 76 (CI-No. 12,245), Basic Violet 1 (CI-No. 42,535), Basic Violet 2, Basic Violet 3 (CI-No. 42,555), Basic Violet 10 (CI-No. 45,170), Basic Violet 14 (CI-No. 42,510), Basic Yellow 57 (CI-No. 12,719), Basic Yellow 87 and Basic Orange 31, and combinations of the named dyes.

One or more dyes from the group HC Blue 15, HC Blue 16 (Blue Quat Bromide), Cationic Blue 347, Basic Violet 2, Basic Red 51, Basic Red 76, Basic Yellow 57, Basic Yellow 87, Basic Orange 31, and Basic Brown 17 have proved particularly suitable.

Most preferably, an agent as contemplated herein contains at least one cationic, direct-acting dye (a) from the group HC Blue 15, HC Blue 16, Basic Red 76, Basic Yellow 57, Basic Orange 31, and Basic Brown 17.

The anionic direct-acting dye(s) (a) are preferably present in a total amount from about 0.001 to about 7% by weight, preferably from about 0.01 to about 5.5% by weight, more preferably from about 0.1 to about 3.4% by weight and particularly preferably from about 0.3 to about 2% by weight, each based on the weight of the colorant.

Further preferred colorants as contemplated herein contain at least one non-ionic direct-acting dye as direct-acting dye (a). This can be selected, for example, from the group HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, HC Blue 15, Disperse Blue 3, HC Violet 1, Disperse Violet 1, Disperse Violet 4, Disperse Black 9, 1,4-diamino-2-nitrobenzene, 2-amino-4-nitrophenol, 1,4-bis(2-hydroxyethyl)-amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and its salts, N,N'-bis(2-hydroxyethyl)-2-nitro-p-phenylenediamine, 2-amino-6-chloro-4-nitrophene ol, 4-ethylamino-3-nitrobenzoic acid and 2-chloro-6-ethylamino-4-nitrophenol.

An agent as contemplated herein comprises at least one non-ionic, direct-acting dye (a) from the group HC Red 1, HC Red 3, HC Red 7, HC Red 13, HC Orange 1, HC Yellow 2, HC Yellow 13, HC Blue 2, HC Blue 11, HC Blue 12, HC Blue 14, HC Violet 2, Disperse Violet 1, 4-[(3-hydroxypropyl)amino]-3-nitrophenol and 4-amino-3-nitrophenol.

The non-ionic direct-acting dye(s) (a) are preferably present in a total amount from about 0.001 to about 7% by weight, preferably from about 0.01 to about 5.5% by weight, more preferably from about 0.1 to about 3.4% by weight and particularly preferably from about 0.3 to about 2% by weight, each based on the weight of the colorant.

Preferred direct-acting dyes (a) to be emphasized are: Basic Red 76, HC Blue 16, Basic Yellow 57, 4-hydroxypropylamino-3-nitrophenol, HC Red 13, HC Red 3, HC Blue 12, HC Orange 1, HC Blue 16 (Blue Quat Bromide), HC Yellow 2, N,N'-bis-(2-hydroxyethyl)-2-nitro-p-phenylenediamine, 4-amino-3-nitrophenol, Ext. D&C Violet 2, HC Violet 2, Basic Brown 17, Basic Red 76 and Basic Yellow 57, and mixtures thereof. More preferred are Basic Red 76, HC Blue 16, Basic Yellow 57, 4-hydroxypropylamino-3-nitrophenol, 4-amino-3-nitrophenol, HC Red 13, HC Violet 2, and mixtures thereof. Particularly preferred are HC Blue 16, Basic Violet 2, Basic Yellow 57, 4-hydroxypropylamino-3-nitrophenol, HC Red 13 and 4-amino-3-nitrophenol and mixtures thereof.

In a preferred embodiment, the agent as contemplated herein comprises a combination of several direct-acting dyes. Nuances can be generated in the entire color spectrum by combining a large number of direct-acting dyes. In this case, both a plurality of purely anionic, purely cationic or purely non-ionic dyes can be combined with each other, and combination of anionic, cationic and/or non-ionic dyes can be used together.

Suitable dyes for combination with one another are, for example, to be selected from HC Red 3, HC Blue 12, HC Orange 1, HC Blue 16 (Blue Quat Bromide), HC Yellow 2, N,N'-bis-(2-hydroxyethyl)-2-nitro-p-phenylenediamine, Ext. D&C Violet 2, Basic Brown 17, Basic Red 76, and Basic Yellow 57.

In general, the combination of several direct-acting dyes applies mutatis mutandis to the amounts specified above of anionic, cationic or non-ionic direct-acting dyes to be used. Even in the case of dye mixtures comprising direct-acting dyes, preference is given to not exceeding the quantities mentioned for the total amounts of direct-acting dyes (a) to be used.

In addition, the agent as contemplated herein contains at least two surfactants, namely at least one amphoteric surfactant (b) and at least one alkyl polyglycoside (c). It has been found that very intense color results could be obtained in particular when the agents as contemplated herein contained, in addition to a direct-acting dye, at least amphoteric surfactant (b) and at least one alkyl polyglycoside (c), wherein the weight-based fraction of amphoteric surfactant, based on the total weight of the agent, is less than the weight-related total amount of alkyl polyglycoside (c) or equal to the weight-related total amount of alkyl polyglycoside (c).

Generally, the total amount of surfactants in the agent as contemplated herein is preferably up to 50% by weight, more preferably from about 1 to about 40% by weight, further preferably from about 5 to about 30% by weight, and most preferably from about 7 to about 12% by weight, in each case based on the weight of the agent.

In a preferred embodiment, the total content, based on the weight of the agent, of amphoteric surfactants (b) and alkyl polyglycosides (c) together is from about 1.0 to about 25.0% by weight, preferably from about 1.5 to about 20.0% by weight, more preferably from about 5.0 to about 15% by weight, and particularly preferably from about 6.0 to about 11.0% by weight.

As previously discussed, particularly advantageous effects have been observed when the agent as contemplated herein comprises by weight less amphoteric surfactant (b) than alkyl polyglycoside (c) or the same amount of amphoteric surfactant (b) as alkyl polyglycoside (c). Preferably, the weight ratio of amphoteric surfactants to alkyl polyglycosides is in the range of from about 1:1 to about 1:30, more preferably in the range of from about 1:1 to about 1:26, especially preferably in the range of from about 1:1 to about 1:20 and in particular in a range of from about 1:1 to about 1:16. If the agent as contemplated herein comprises less amphoteric surfactants (b) than alkyl polyglycosides (c) based on its weight, the weight ratio of amphoteric surfactants to alkyl polyglycosides is preferably in a range of from about 1:1.1 to about 1:30, more preferably in a range of from about 1:1.5 to about 1:26, especially preferably from about 1:2 to about 1:20 and in particular in a range of from about 1:3 to about 1:16. The total amount of amphoteric surfactants and alkyl polyglycosides is used in each case to calculate the weight ratio.

In one embodiment, the weight-related total amount of amphoteric surfactant (b) in the agent equals the weight-related total amount of alkyl polyglycoside (c). In an alternative embodiment, the weight-related total amount of amphoteric surfactant (b) in the agent is less than the weight-related total amount of alkyl polyglycoside (c).

Based on the total weight of the agent, the total amount of at least one amphoteric surfactant (b) is preferably from about 0.5 to about 15.0% by weight, more preferably from about 0.5 to about 7.0% by weight, particularly preferably from about 1.0 to about 6.0% by weight and in particular from about 1.3 to about 4.0% by weight.

Based on the total weight of the agent, the total amount of at least one alkyl polyglycoside (c) is preferably from about 0.5 to about 15.0% by weight, more preferably from about 2.0 to about 14.0% by weight, particularly preferably from about 3.0 to 1 about 3.0% by weight, exceptionally preferably from about 4.0 to about 10.0% by weight, and in particular from about 6.0 to about 8.0% by weight.

In a preferred embodiment, the colorant as contemplated herein contains, based on its weight, at least one amphoteric surfactant (b) in a total amount of from about 0.5 to about 15.0% by weight and at least one alkyl polyglycoside (c) in a total amount of from about 0.5 to about 15.0% by weight, with the proviso that agents as contemplated herein contain less amphoteric surfactant (b) than alkyl polyglycoside (c) or contain the same amount of amphoteric surfactant (b) as alkyl polyglycoside (c), wherein the weight ratio of amphoteric surfactants to alkyl polyglycosides is preferably in a range of from about 1 to about 1:30, more preferably in a range of from about 1:1.1 to about 1:20, yet more preferably in a range of from about 1:2 to about 1:10 and in particular in a range of from about 1:4 to about 1:6. These weight ratios are based on the total amount of amphoteric surfactants and the total amount of alkyl polyglycosides.

In a preferred embodiment, the colorant as contemplated herein contains, based on its weight, at least one amphoteric surfactant (b) in a total amount of from about 0.5 to about 7.0% by weight and at least one alkyl polyglycoside (c) in a total amount of from about 2.0 to about 14.0% by weight, with the proviso that agents as contemplated herein contain less amphoteric surfactant (b) than alkyl polyglycoside (c) or contain the same amount of amphoteric surfactant (b) as alkyl polyglycoside (c), wherein the weight ratio of amphoteric surfactants to alkyl polyglycosides is preferably in a range of from about 1 to about 1:30, more preferably in a range of from about 1:1.1 to about 1:20, yet more preferably in a range of from about 1:2 to about 1:10 and in particular in a range of from about 1:4 to about 1:6. These weight ratios are based on the total amount of amphoteric surfactants and the total amount of alkyl polyglycosides.

In a further preferred embodiment, the colorant as contemplated herein contains, based on its weight, at least one amphoteric surfactant (b) in a total amount of from about 1.0 to about 6.0% by weight, preferably from about 1.3 to about 4.0% by weight, and at least one alkyl polyglycoside (c) in a total amount of from about 3.0 to about 13.0% by weight, preferably from about 4.0 to about 10.0% by weight, and most preferably from about 6.0 to about 8.0% by weight, with the proviso that agents as contemplated herein contain less amphoteric surfactant (b) than alkyl polyglycoside (c) or the same amount of amphoteric surfactant (b) as alkyl polyglycoside (c), wherein the weight ratio of amphoteric surfactant to alkyl polyglycoside is preferably in a range of from about 1 to about 1:30, more preferably in a range of from about 1:1.1 to about 1:20, yet more preferably in a range of from about 1:2 to about 1:10, and in particular in a range of from about 1:4 to about 1:6. These weight ratios are based on the total amount of amphoteric surfactants and the total amount of alkyl polyglycosides.

As was previously explained, amphoteric surfactants (b) in the hydrophilic molecular component comprise at least one negatively charged and at least one positively charged group. Examples of preferred amphoteric surfactants are the betaines, the N-alkyl-N,N-dimethylammonium glycinates, the N-acylaminopropyl-N,N-dimethylammonium glycinates and the 2-alkyl-3-carboxymethyl-3-hydroxyethyl-imidazolines each having from about 8 to about 24 carbon atoms in the alkyl group.

In a preferred embodiment, at least one betaine, in particular at least one alkyl betaine, is used as an amphoteric surfactant (b). This is particularly preferably an alkyl amido alkyl betaine of the following formula (I):

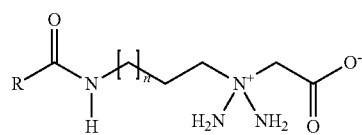

(I)

wherein

R represents a linear or branched, saturated or unsaturated hydrocarbon radical having from about 5 to about 20, preferably from about 8 to about 14, carbon atoms, and n is an integer from 0 to about 10, in particular from 0 to about 4.

In a preferred embodiment, R is a linear hydrocarbon radical, in particular a linear, saturated hydrocarbon radical.

In a very particularly preferred embodiment, an alkyl amido alkyl betaine of the formula (I) with R=—C10H21, —C11H23 or —C12H25 and n=0, 1 or 2 is used, in particular an alkyl amido alkyl betaine of the formula (I) with R=—C11H23 and n=1 is used as an amphoteric surfactant (b), also known as cocamidopropyl betaine.

Preferably, the aqueous commercial product preparation of the amphoteric surfactant (b) is substantially free of sodium chloride, that is, it comprises <0.5% by weight, preferably <0.4% by weight, particularly preferably <0.2% by weight of sodium chloride, each based on the total weight of the aqueous commercial product preparation of the amphoteric surfactant (b).

High purity sodium chloride-poor cocamidopropyl betaine having an active substance content of 35% by weight of cocamidopropyl betaine and a sodium chloride content of <0.5% by weight is available, for example, under the tradename EMPIGEN® Total Active TC/U from Huntsman Corporation.

The alkyl polyglycosides (c) are non-ionic surfactants exemplified by the absence of electrical charges in the molecules.

Alkyl polyglycosides as contemplated herein are distinguished by having a hydrophobic, long-chain alkyl radical and a glycoside sugar as a hydrophilic molecular component. In a preferred embodiment, the alkyl polyglycoside comprises at least one linear, branched or cyclic, saturated or unsaturated having from about 1 to about 30 carbon atoms, preferably from about 5 to about 25 carbon atoms and in particular from about 8 to about 20 carbon atoms. Most preferably, the alkyl radical is linear and more preferably linear and saturated. The degree of polymerization of the glycoside sugar is preferably from about 1 to about 10, in particular from about 1 to about 5, particularly preferably from about 1.1 to about 2.

Particularly preferred alkyl polyglycosides are alkyl polyglucosides.

Particularly preferred alkyl polyglucosides comprise lauryl polyglucoside, decylpoly glucoside, octyl polyglucoside and coco glucoside, in particular lauryl polyglucoside.

Preferably, the aqueous commercial product preparation of the alkyl polyglycoside (c) is substantially free of sodium chloride, that is, it comprises <0.5% by weight, preferably <0.4% by weight, particularly preferably <0.2% by weight of sodium chloride, in each case based on the total weight of the aqueous commercial product preparation of the alkyl polyglycoside (c). Lauryl polyglycoside is available, for example, under the trade name PLANTACARE® from BASF SE.

In a particularly preferred embodiment, the colorant as contemplated herein is substantially free of sodium chloride, that is, it comprises <0.2% by weight, in particular <0.1% by weight, more preferably <0.05% by weight, particularly preferably <0.02% by weight, exceptionally preferably 0.005 to 0.015% by weight of sodium chloride, more preferably 0% by weight sodium chloride, each based on the total weight of the colorant.

In a particularly preferred embodiment of the disclosure, the agent comprises, for dyeing keratinic fibers, in particular human hair, containing in a cosmetic carrier (a) at least one direct-acting dye,
(b) at least one alkyl amido alkyl betaine of formula (I), preferably cocamidopropyl betaine $(C_{11}H_{23})C(O)NH(C_3H_6)N(NH_2)_2CH_2C(O)O$, and
(c) at least one alkyl polyglycoside, preferably lauryl glycoside, with the proviso that the agent is substantially free of sodium chloride, wherein the weight-related total amount of amphoteric surfactant (b) in the agent, based on the weight of the agent, is less than the weight-related total amount of alkyl polyglycoside (c) or equal to the weight-related total amount of alkyl polyglycoside (c).

The treatment of keratinic fibers with agents which contain (a) at least one direct-acting dye, (b) at least one amphoteric surfactant, and (c) at least one non-ionic surfactant resulted in particularly intense colorings in attractive nuances. In this case, it has surprisingly been found that the color lift ability by using the combination of an amphoteric surfactant (b) and an alkyl polyglycoside (c) in a weight ratio of from about 1 to about 1:30, more preferably in a range of from about 1:1.1 to about 1:20, particularly preferably in a range from about 1:2 to about 1:10 and in particular in a range from about 1:4 to about 1:6, could be further optimized. Particularly intensive colorings were obtained when at least one amphoteric surfactant (b) from the group of the alkyl amido alkyl betaines and at least one alkyl polyglycoside (c) from the group of the alkyl polyglucosides were used in the colorants in addition to the direct-acting dyes (a).

In a particularly preferred embodiment, an agent as contemplated herein contains (b) at least one amphoteric surfactant selected from the group of the alkyl amido alkyl betaines of the formula (I), in particular cocamidopropyl betaine ((C11H23)C(O)NH(C3H6)N(NH2)2CH2C(O)O).

Furthermore, particularly good results have been achieved in which the surfactant preparations (b) and (c) are substantially free of sodium chloride. The colorant as contemplated herein particularly preferably comprises <0.2% by weight of NaCl, in particular <0.1% by weight of NaCl. Preferably, the entire agent is free of NaCl.

The colorants can further contain additional active ingredients, auxiliaries and additives in order to improve the dyeing performance and to adjust other desired properties of the agents. The colorants are preferably provided as a liquid preparation and, if appropriate, an additional surface-active substance is additionally added to the agents, wherein such surface-active substances are referred to as surfactants or as emulsifiers, depending on the field of application: They are preferably selected from sulfate-free anionic, cationic, non-ionic, ampholytic and amphoteric surfactants and emulsifiers.

As was already explained above, cationic surfactants are understood to be surfactants, that is, surface-active compounds, each having one or more positive charges. Cationic surfactants contain only positive charges. Usually, these surfactants are made of a hydrophobic part and a hydrophilic head group, wherein the hydrophobic part usually of a hydrocarbon skeleton (e.g., including one or two linear or branched alkyl chains), and the positive charge(s) are located in the hydrophilic head group. Cationic surfactants adsorb at boundary surfaces and aggregate in aqueous solution above the critical micelle concentration to positively charged micelles.

Examples of cationic surfactants suitable as contemplated herein are:
quaternary ammonium compounds which as hydrophobic radicals can carry one or two alkyl chains having a chain length of from about 8 to about 28 C atoms,
quaternary phosphonium salts substituted with one or more alkyl chains having a chain length of from about 8 to about 28 C atoms, or
tertiary sulfonium salts.

Furthermore, the cationic charge can also be in the form of an onium structure constituent of a heterocyclic ring (e.g., an imidazolium ring or a pyridinium ring). In addition to the functional unit which carries the cationic charge, the cationic surfactant can also contain further uncharged functional groups, such as is the case with esterquats. Cationic surfactants of this type are, for example, physiologically compatible salts of N,N,N-trimethyl-1-hexadecanaminium, in particular N,N,N-trimethyl-1-hexadecanaminium chloride, which is also sold under the trade name Dehyquart A-CA. Another suitable cationic surfactant is a physiologically compatible salt of dimethyldistearyldimethylammonium, more preferably dimethyldistearylammonium chloride. Further cationic surfactants can be selected from the group of cationic imidazolium compounds.

Examples of preferred ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, wherein the ampholytic surfactant is different from the amphoteric surfactant (b).

The one or more ampholytic and/or cationic surfactants are preferably present in a total amount of from about 0.0 to about 5.0% by weight, preferably from about 0.1 to about 2.5% by weight, more preferably from about 0.4 to about 1.8% by weight and particularly preferably from about 0.6 to about 0.9% by weight, each based on the total weight of the agent.

For anionic surfactants, the hydrophilic molecular component comprises at least one negatively charged hydrophilic head group. The negatively charged hydrophilic head group can be, for example, a carboxylic acid group or the salt of a carboxylic acid group, a sulfonic acid group or the salt of the sulfonic acid group, a sulfuric acid ester grouping or the salt thereof, a phosphonic acid group or the salt of the phosphonic acid group, or a phosphoric acid ester grouping or the salt thereof.

The cosmetic agent as contemplated herein usually comprises an aqueous carrier. In aqueous solution, the above-mentioned hydrophilic head groups of the anionic surfactant, such as the carboxylic acid and the salts of the carboxylic acids, are present in an equilibrium whose position is determined by the pH of the agent. If, for example, a fatty acid is used as the anionic surfactant, then a small part of the fatty acid is present in aqueous solution in the form of the protonated fatty acid, whereas the major part of the fatty acid is deprotonated in aqueous solution and converted in this way into the salt of the fatty acid. For this reason, the definition of an anionic surfactant also includes a surfactant having a, still protonated, acid group. An anionic surfactant in the context of the present disclosure contains no cationic groupings, that is, amphoteric surfactants are not included in the definition of an anionic surfactant.

Anionic surfactants are therefore exemplified by the presence of a water-solubilizing, anionic group such as a carboxylate, sulfate, sulfonate or phosphate group and a lipophilic alkyl group having about 8 to about 30 carbon atoms. In addition, glycol or polyglycol ether groups, ester, ether and amide groups and hydroxyl groups can be present in the molecule.

Typical examples of anionic surfactants are alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and their salts, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (in particular wheat-based vegetable products) and alkyl (ether) phosphates. If the anionic surfactants contain polyglycol ether chains, these can have a conventional, but preferably a narrow homolog distribution.

Anionic surfactants, in particular sulfated surfactants, that is, anionic surfactants which comprise at least one sulfate group (—OSO3), generally have a negative influence on the color lift of direct-acting dyes, in particular cationic, direct-acting dyes. In a particularly preferred embodiment, the agent as contemplated herein therefore comprises only small amounts of surfactants which comprise a sulfate group, in particular alkyl sulfates and alkyl ether sulfates such as fatty alcohol ether sulfates, glycerol ether sulfates, hydroxy mixed ether sulfates, monoglyceride (ether) sulfates, fatty acid amide (ether) sulfates. The agent as contemplated herein preferably contains sulfate group-containing surfactants in a total amount of from 0 to ≤0.2% by weight, preferably from 0 to ≤0.15% by weight and in particular from 0 to ≤0.1% by weight, based on the weight of the agent. Most preferably, the agent is free of sulfate-containing surfactants.

In a further, particularly preferred embodiment, the agent as contemplated herein comprises only small amounts of anionic surfactants. The agent as contemplated herein preferably comprises anionic surfactants in a total amount of preferably from 0 to ≤0.2% by weight, more preferably from 0 to ≤0.15% by weight, and in particular from 0 to ≤0.1% by weight, based on the total weight of the agent. Most preferably, the agent is free of anionic surfactants.

In a further, particularly preferred embodiment, the agent as contemplated herein comprises as surfactants exclusively the at least one amphoteric surfactant (b) in combination with the at least one non-ionic surfactant (c).

The ready-to-use agents can contain further auxiliaries and additives. Dyeing processes on keratin fibers usually take place in the weakly acidic to alkaline range, preferably in the slightly acidic to weakly alkaline medium. However, in order to preserve the keratin fibers and the skin as much as possible, it is not desirable to set too high a pH.

In principle, the pH value of the agent can be in the range from about pH 2 to about pH 11, preferably in the range from about pH 3 to about pH 8. In a further very particularly preferred embodiment, an agent as contemplated herein has a pH value in the range from about 2 to about 11, preferably from about 3 to about 8, more preferably from about 3.5 to about 7.0, yet more preferably from about 4.0 to about about 6.5, and most preferably from 4.5 to about 5.5.

The measurement of the pH value can be carried out, for example, with a glass electrode, which is usually designed in the form of a single-rod measuring cell. The pH values of the present disclosure are pH values that were measured at a temperature of 22° C.

The alkalizing agents which can be used as contemplated herein for adjusting the preferred pH can be selected from the group that is formed from ammonia, alkanolamines, basic amino acids and inorganic alkalizing agents such as (earth) alkali metal hydroxides, (earth) alkali metal metasilicates, (earth) alkaline metal phosphates and (earth) alkali metal hydrogen phosphates. Preferred inorganic alkalizing agents are magnesium carbonate, sodium hydroxide, potassium hydroxide, sodium silicate and sodium metasilicate.

Organic alkalizing agents which can be used as contemplated herein are preferably selected from monoethanolamine, 2-amino-2-methylpropanol and triethanolamine. The basic amino acids which can be used as alkalizing agents as contemplated herein are preferably selected from the group that is formed from arginine, lysine, ornithine and histidine, more preferably arginine. However, it has been found in the context of the investigations on the present disclosure that further preferred agents as contemplated herein additionally contain an organic alkalizing agent. An embodiment of the first subject of the disclosure additionally contains at least one alkalizing agent which is selected from the group that is formed from ammonia, alkanolamines and basic amino acids, in particular ammonia, monoethanolamine and arginine or its compatible salts.

Acidifying agents which can be used to adjust the pH value are organic acids, such as citric acid, acetic acid, ascorbic acid, benzoic acid, lactic acid, malic acid and maleic acid, and mineral acids, such as hydrochloric acid, sulfuric acid or phosphoric acid.

Furthermore, it has proven to be advantageous when the colorants contain at least one stabilizer or complexing agent. Particularly preferred stabilizers are phenacetin, alkali benzoates (sodium benzoate) and salicylic acid. Furthermore, all complexing agents of the prior art can be used. Preferred complexing agents as contemplated herein are nitrogen-containing polycarboxylic acids, in particular EDTA and EDDS, and phosphonates, in particular 1-hydroxyethane-1, 1-diphosphonate (HEDP) and/or ethylenediamine tetramethylenephosphonate (EDTMP) and/or diethylenetriamine-pentamethylenephosphonate (DTPMP) or their sodium salts.

Furthermore, the agents as contemplated herein can contain further active ingredients, auxiliaries and additives, for example non-ionic polymers such as vinylpyrrolidinone/vinyl acrylate copolymers, polyvinylpyrrolidinone, vinylpyrrolidinone/vinyl acetate copolymers, polyethylene glycols and polysiloxanes; silicones such as volatile or nonvolatile, straight-chain, branched or cyclic, crosslinked or uncrosslinked polyalkylsiloxanes (such as dimethicones or cyclomethicones), polyarylsiloxanes and/or polyalkylarylsiloxanes, in particular polysiloxanes having organofunctional groups, such as substituted or unsubstituted amines (amodimethicones), carboxyl, alkoxy and/or hydroxyl groups (dimethicone copolyols), linear polysiloxane A) polyoxyalkylene B) block copolymers, grafted silicone polymers; cationic polymers such as quaternized cellulose ethers, polysiloxanes having quaternary groups, dimethyldiallylammonium chloride polymers, acrylamide-dimethyldiallylammonium chloride copolymers, with diethyl sulfate quaternized dimethylaminoethyl methacrylate-vinylpyrrolidinone copolymers, vinylpyrrolidinone-imidazolinium methochloride copolymers and quaternized polyvinyl alcohol; zwitterionic and amphoteric polymers; anionic polymers such as polyacrylic acids or crosslinked polyacrylic acids; fatty substances such as C8-C30 fatty alcohols, hydrocarbons or natural oils and fats; hair conditioning compounds such as phospholipids, for example, lecithin and cephalins; perfume oils, dimethylisosorbide and cyclodextrins; fiber-structure-improving active ingredients, in particular mono-, di- and oligosaccharides such as glucose, galactose, fructose, fruit sugar and lactose; dyes for staining the agent; anti-dandruff active ingredients such as piroctone olamine, zinc omadine and climbazole; amino acids and oligopeptides; protein hydrolyzates based on animal and/or vegetable, and in the form of their fatty acid condensation products or optionally anionically or cationically modified derivatives; sunscreens and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescing agents such as ethylene glycol mono- and distearate and PEG-3-distearate and pigments.

The selection of these further substances is made by the person skilled in the art according to the desired properties of the agents. With regard to further optional components and the amounts of these components used, reference is expressly made to the relevant manuals known to the person skilled in the art. The additional active ingredients and auxiliaries are preferably used in the agents as contemplated herein in amounts of from about 0.0001 to about 25% by weight, in particular from about 0.0005 to about 15% by weight, based on the total weight of the respective agents.

The agents as contemplated herein contain the direct-acting dyes in combination with at least one amphoteric surfactant (b) and at least one non-ionic surfactant (c) in a cosmetic carrier. This cosmetic carrier is preferably aqueous, alcoholic or aqueous-alcoholic. For the purpose of hair treatment, such carriers are, for example, creams, emulsions, gels or surfactant-containing foaming solutions, such as shampoos, foam aerosols or other preparations which are suitable for use on the hair. Particularly suitable are shampoos (tinting shampoos).

In the context of the disclosure, an aqueous carrier contains at least about 40% by weight, in particular at least about 50% by weight, of water. In the context of the present disclosure, aqueous-alcoholic carriers are understood to mean water-containing compositions containing from about 3 to about 70% by weight of a C1-C4 alcohol, in particular ethanol or isopropanol. The agents as contemplated herein can additionally contain further organic solvents such as 4-methoxybutanol, ethyl diglycol, 1,2-propylene glycol, n-propanol, n-butanol, 1,3-butylene glycol, glycerol, diethylene glycol monoethyl ether, and diethylene glycol mono-n-butyl ether. Preference is given to all water-soluble organic solvents. Preferred agents as contemplated herein additionally contain a non-aqueous solvent, wherein preferred agents as contemplated herein contain the non-aqueous solvent in a concentration of from about 0.1 to about 30% by weight, preferably in a concentration of from about 1 to about 20% by weight, completely particularly preferably in a concentration of from about 2 to about 10% by weight, each based on the total weight of the agent.

In addition, at least one penetration enhancer can also be included. Penetration enhancers can usually also function as solvents. Exemplary of suitable penetration enhancers can be mentioned here propylene carbonate, benzyl alcohol, 2-phenoxyethane-1-ol and/or benzyl alcohol.

In a further very particularly preferred embodiment, an agent as contemplated herein additionally contains at least one penetration enhancer from the group of propylene carbonate, benzyl alcohol, 2-phenoxyethane-1-ol and/or benzyl alcohol.

It is particularly advantageous when the colorant as contemplated herein contains at least one penetration enhancer from the group of benzyl alcohol, 2-phenoxyethane-1-ol and/or propylene carbonate. The color lift of the acid dyes can be increased disproportionately by using one or more solvents from this group. Furthermore, it has been found that the fastness properties of the colorings obtainable with the agent as contemplated herein are better.

If keratinic fibers are dyed with an agent containing at least one of the two aromatic alcohols, colorings, which are exemplified by very good gray coverage, are then obtained in a subsequent coloring with substantive acid dyes. The wash fastness of these colorings is also outstanding.

The agent as contemplated herein can preferably contain the solvent(s) in certain total amounts in the range from about 0 to about 20.0% by weight, preferably from about 1.0 to about 17.0% by weight, more preferably from about 5.0 to about 14.0% by weight and most preferably from about 8.5 to about 12.5% by weight, based in each case on the weight of the colorant as contemplated herein.

As was already stated, the agent is preferably provided as a liquid preparation. It has proved to be advantageous when the agents contain at least one thickener. There are no fundamental restrictions with regard to these thickeners. Both organic and purely inorganic thickeners can be used.

Suitable thickeners are anionic, synthetic polymers; cationic, synthetic polymers; naturally occurring thickeners such as non-ionic guar gums, scleroglucan gums or xanthan gums, gum arabic, ghatti gum, karaya gum, gum tragacanth, carrageenan gum, agar agar, locust bean gum, pectins, alginates, starch fractions and derivatives such as amylose, amylopectin and dextrins, and cellulose derivatives such as methylcellulose, carboxyalkylcelluloses and hydroxyalkylcelluloses; non-ionic, fully synthetic polymers, such as polyvinyl alcohol or polyvinylpyrrolidinone; and inorganic thickeners, in particular phyllosilicates such as bentonite, in particular smectites, such as montmorillonite or hectorite.

Particular preference is given to associative thickeners such as hydrophobically modified polyacrylates (HASE), hydrophobically modified cellulose ethers (HMHEC), hydrophobically modified polyacrylamides (HMPAM), hydrophobically modified polyethers (HMPE) and associative polyurethane thickeners. Particularly preferred are hydrophobically modified cellulose ethers, in particular C5-C25 alkylhydroxyethylcellulose, preferably C10-C20 alkylhydroxyethylcellulose, for example C14 alkylhydroxyethylcellulose, C15 alkylhydroxyethylcellulose, C16 alkylhydroxyethylcellulose, C17 alkylhydroxyethylcellulose, C18 alkylhydroxyethylcellulose, and mixtures thereof.

Particularly preferred is cetyl hydroxyethyl cellulose, available under the trade name Natrosol™ Plus 330 CS from Ashland.

Preferably, at least one thickener is present in a total amount of from about 0.1 to about 5% by weight, particularly preferably from about 0.1 to about 3% by weight, more preferably from about 0.1 to about 2% by weight, yet more preferably from about 0.2 to about 1.5% by weight and in particular from about 0.5 to about 1% by weight, each based on the weight of the agent.

The agent as contemplated herein can also contain anionic polymeric thickeners. Suitable compounds are, for example, selected from the crosslinked or uncrosslinked copolymers which contain at least two different monomers from the group of acrylic acid, methacrylic acid, the C1-C6 alkyl esters of acrylic acid and/or the C1-C6 alkyl esters of methacrylic acid. Particularly preferred anionic copolymers are copolymers of acrylic acid, methacrylic acid or their C1-C6 alkyl esters, which are sold under the INCI name Acrylates Copolymer. Particularly preferred is the combination of methacrylic acid and ethyl acrylate and optionally crosslinking, multifunctional monomers. A preferred commercial product for this is, for example, Aculyn® 33 or 33A, which is offered by Rohm & Haas. A further preferred anionic polymeric thickener is polyacrylate-1 crosspolymer, a copolymer of at least one C1-C6 alkyl ester of acrylic acid or of methacrylic acid, C1-4 dialkylamino-C1-6 alkyl methacrylate, PEG/PPG-30/5 allyl ether, PEG 20-25 C10-30 alkyl ether methacrylate and hydroxy C2-6 alkyl methacrylate that is crosslinked with ethylene glycol dimethacrylate.

Furthermore, the agent as contemplated herein contains as a film former one or more cationic compounds from the group Polyquaternium-1, Polyquaternium-2, Polyquaternium-3, Polyquaternium-4, Polyquaterium-5, Polyquaternium-6, Polyquaternium-7, Polyquaternium-8, Polyquaternium-9, Polyquaternium-10, Polyquaternium-11, Polyquaternium-14, Polyquaternium-16, Polyquaternium-17, Polyquaternium-18, Polyquaternium-22, Polyquaternium-24, Polyquaternium-27, Polyquaternium-28, Polyquaternium-32, Polyquaternium-33, Polyquaternium-37, Polyquaternium-39, Polyquaternium-44, Polyquaternium-46, Polyquaternium-53, Polyquaternium-55, Polyquaternium-64, Polyquaternium-67, Polyquaternium-68, Polyquaternium-69 and/or Polyquaternium-86 as a film former.

Polyquaternium-37 is emphasized as a particularly preferred film former. This improves the properties of the agent and the quality of the coloring obtained.

Preferred is at least one cationic polyquaternium compound in a total amount of from about 0.1 to about 5% by weight, particularly preferably from about 0.2 to about 3% by weight, more preferably from about 0.3 to about 2% by weight and in particular in an amount from about 0.5 to about 1% by weight, each based on the weight of the agent.

At least one associative thickener, in particular a hydrophobically modified cellulose ether, and at least one polyquaternium compound are preferably used in combination with one another. Particularly good color results could be achieved with a combination of cetyl hydroxyethyl cellulose and Polyquaternium-37.

Furthermore, hair conditioning compounds can preferably be included in the agents. Hair conditioning compounds have, for example, due to cationic or cationizable groups, in particular protonated amine groups or quaternary ammonium groups, a substantivity to human hair. Particularly preferred hair conditioning compounds are cationic and/or amphoteric polymers.

The agent as contemplated herein can be formulated in various forms. Thus, it can be applied, for example, as a gel, as an emulsion, as a solution or in the form of a dyeing foam. The use of gels (shampoo) represents a particularly appealing and comfortable form of application for the user and is therefore preferred. The gel can be applied directly to the keratinic fibers to be dyed and the application process can be easily integrated into the everyday hygiene of the user. Therefore, the formulation of the agent as a shampoo (tinting shampoo) is particularly preferred.

The subject of the present disclosure is therefore also an agent for modifying keratinic fibers, in particular human hair, containing in a cosmetic carrier in the form of a shampoo
(a) at least one direct-acting dye,
(b) at least one amphoteric surfactant, in particular at least one alkyl betaine,
(c) at least one alkyl polyglycoside, in particular at least one alkyl polyglucoside,
(d) water and
(e) at least one thickener,
preferably with the proviso that the agent is substantially free of sodium chloride,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c).

A further subject of the present disclosure is also an agent for modifying keratinic fibers, in particular human hair, containing in a cosmetic carrier in the form of a shampoo
(a) at least one direct-acting dye,
(b) at least one amphoteric surfactant, in particular at least one alkyl betaine,
(c) at least one alkyl polyglycoside, in particular at least one alkyl polyglucoside,
(d) water,
(e) at least one thickener, and
(f) at least one film former,
preferably with the proviso that the agent is substantially free of sodium chloride,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c).

The agents as contemplated herein are formulated as one-component agents and are used accordingly, that is, they are removed directly from a packaging container in which they were prepared, and applied to the keratinic fibers.

Further subject of the present disclosure is the use of an agent containing in a cosmetic carrier,
(a) at least one direct-acting dye,
(b) at least one amphoteric surfactant, in particular at least one alkyl betaine, and
(c) at least one alkyl polyglycoside, in particular at least one alkyl polyglucoside,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c), for
 Increasing the chromaticity of the dyes on the keratinic fiber and/or
 Increasing the color lift of the dyes on the keratinic fiber and/or
 Increasing the color intensity of the dyes on the keratinic fiber
in the coloring of keratinic fibers, in particular human hair.

What is said about the agent applies mutatis mutandis with respect to further preferred embodiments of the use.

The agent of the subject disclosure can be used in methods for dyeing human hair.

A further subject of the present disclosure is therefore a method for
 Increasing the chromaticity of the dyes on the keratinic fiber and/or
 Increasing the color lift of the dyes on the keratinic fiber and/or
 Increasing the color intensity of the dyes on the keratinic fiber.
in the coloring of human hair, in which an agent containing in a cosmetic carrier
(a) at least one direct-acting dye,
(b) at least one amphoteric surfactant, in particular at least one alkyl betaine, and (c) at least one alkyl polyglycoside, in particular at least one alkyl polyglucoside,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c),
is applied to the keratinic fibers.

What has been said about the agent and uses applies mutatis mutandis with regard to further preferred embodiments of the method.

In summary, the present disclosure is outlined in particular by the following points:

Agent for the dyeing of keratinic fibers, in particular human hair, containing in a cosmetic carrier
(a) at least one direct-acting dye,
(b) at least one amphoteric surfactant, in particular at least one alkyl betaine, and
(c) at least one alkyl polyglycoside, in particular at least one alkyl polyglucoside,
wherein the weight-related total amount of amphoteric surfactant (b) in the agent, based on the weight of the agent, is less than the weight-related total amount of alkyl polyglycoside (c) or equal to the weight-related total amount of alkyl polyglycoside (c).

Agent as described above, wherein the total content of amphoteric surfactant (b) and alkyl polyglycoside (c) together, based on the total weight of the agent, amounts to from about 1.0 to about 25.0% by weight, preferably from about 1.5 to about 20.0% by weight.

Agent as described above, wherein the agent, based on its total weight, contains at least one amphoteric surfactant (b) in a total amount of from about 0.5 to about 15.0% by weight, preferably from about 0.5 to about 7.0% by weight, particularly preferably from about 1.0 to about 6.0% by weight and in particular from about 1.3 to about 4.0% by weight.

Agent as described above, wherein the agent, based on its total weight, contains at least one alkyl polyglycoside (c) in a total amount of from about 0.5 to about 15.0% by weight, preferably from about 2.0 to about 14.0% by weight, in particular preferably from about 3.0 to about 13.0% by weight, most preferably from about 4.0 to about 10.0% by weight, and in particular from about 6.0 to about 8.0% by weight.

Agent as described above, wherein the amphoteric surfactant (b) is an alkyl betaine, preferably an alkylamidoalkyl betaine, in particular a C8-14 alkylamido-(C2-6) alkyl betaine.

Agent as described above, wherein the alkyl polyglycoside (c) is an alkyl polyglycoside, preferably an alkyl polyglycoside having an alkyl radical comprising about 10 to about 20 carbon atoms.

Agent as described above, wherein the amphoteric surfactant (b) is an alkyl amido alkyl betaine, preferably cocamidopropyl betaine ((C11H23)C(O)NH(C3H6)N(NH2)2CH2C(O)O), and the alkyl polyglycoside (c) is an alkyl polyglucoside, preferably lauryl glucoside.

Agent as described above, wherein the at least one direct-acting dye is selected from a cationic direct-acting dye, an anionic direct-acting dye or a non-ionic direct-acting dye or mixtures thereof.

Agent as described above, wherein the at least one direct-acting dye is selected from HC Blue 16, Basic Violet 2, Basic Yellow 57, 4-hydroxypropylamino-3-nitrophenol, HC Red 13 and 4-amino-3-nitrophenol and mixtures thereof.

Agent as described above, wherein the agent has a pH value from about 2 to about 11, preferably from about 3 to about 8, more preferably from about 3.5 to about 7.0, yet more preferably from about 4.0 to about 6.5, and most preferably from about 4.5 to about 5.5, each measured at 22° C.

Agent as described above, wherein the agent further contains ≤0.2% by weight, based on the total weight of the agent, of surfactants which include a sulfate group (—OSO3).

Agent as described above, wherein the agent comprises ≤0.2% by weight, based on the total weight of the agent, of anionic surfactants.

Agent as described above, wherein the agent further comprises at least one associative thickener, preferably a non-ionic associative thickener, in particular cetylhydroxyethylcellulose, preferably in an amount, based on the total weight of the agent, from about 0.1 to about 5% by weight.

Agent as described above, wherein the agent further comprises at least one film former, in particular Polyquaternium-37, preferably in an amount, based on the total weight of the agent, from about 0.1 to about 5% by weight.

Agent as described above, wherein the agent comprises at least one non-ionic associative thickener, in particular cetylhydroxyethylcellulose, and at least one cationic polymer, in particular Polyquaternium-37, in combination with one another.

Agent for dyeing keratinic fibers, in particular human hair, containing in a cosmetic carrier in the form of a shampoo
(a) at least one direct-acting dye,
(b) at least one amphoteric surfactant, in particular at least one alkyl betaine,
(c) at least one, in particular at least one alkyl polyglucoside,
(d) water and
(e) at least one thickener,
preferably with the proviso that the agent is substantially free of sodium chloride,
wherein the weight-related total amount of amphoteric surfactant (b) in the agent, based on the total weight of the agent, is less than the weight-related total amount of alkyl polyglycoside (c) or equal to the weight-related total amount of alkyl polyglycoside (c).

Agent for dyeing keratinic fibers, in particular human hair, containing in a cosmetic carrier in the form of a shampoo
(a) at least one direct-acting dye,
(b) at least one amphoteric surfactant, in particular at least one alkyl betaine,
(c) at least one alkyl polyglycoside, in particular at least one alkyl polyglucoside,
(d) water,
(e) at least one thickener, and
(f) at least one film former,
preferably with the proviso that the agent is substantially free of sodium chloride,
wherein the weight-related total amount of amphoteric surfactant (b) in the agent, based on the total weight of the agent, is less than the weight-related total amount of alkyl polyglycoside (c) or equal to the weight-related total amount of alkyl polyglycoside (c).

Use of an agent containing in a cosmetic carrier
(a) at least one direct-acting dye,
(b) at least one amphoteric surfactant, in particular at least one alkyl betaine, and
(c) at least one alkyl polyglycoside, in particular at least one alkyl polyglucoside,
wherein the weight-related total amount of amphoteric surfactant (b) in the agent, based on the total weight of the agent, is less than the weight-related total amount of alkyl polyglycoside (c) or equal to the weight-related total amount of alkyl polyglycoside (c) for Increasing the chromaticity of the dyes on the keratinic fiber and/or Increasing the color lift of the dyes on the keratinic fiber and/or Increasing the color intensity of the dyes on the keratinic fiber.

in the coloring of keratinic fibers, in particular human hair.

Method for

Increasing the chromaticity of the dyes on the keratinic fiber and/or

Increasing the color lift of the dyes on the keratinic fiber and/or

Increasing the color intensity of the dyes on the keratinic fiber.

in the coloring of keratinic fibers, in particular human hair, in which an agent containing in a cosmetic carrier (a) at least one direct-acting dye, (b) at least one amphoteric surfactant, in particular at least one alkyl betaine, and (c) at least one alkyl polyglycoside, in particular at least one alkyl polyglucoside, wherein the weight-related total amount of amphoteric surfactant (b) in the agent, based on the total weight of the agent, is less than the weight-related total amount of alkyl polyglycoside (c) or equal to the weight-related total amount of alkyl polyglycoside (c).

is applied to the keratinic fibers.

The colorants as contemplated herein are exemplified by good foaming properties, which are comparable to classic shampoos. Foaming degrees of more than about 2 cm can be achieved (rapid foaming test in the beaker).

The colorants contemplated herein enable the formulation of tinting shampoos which simultaneously comprise anionic, cationic and non-ionic direct-acting dyes and utilize the full coloring power of each dye.

The use of the specific combination of amphoteric surfactants (b) and alkyl polyglycoside (c), wherein the weight-related total amount of amphoteric surfactant (b) in the agent, based on the total weight of the agent, is less than the weight-related total amount of alkyl polyglycoside (c) or equal to the weight-related total amount of alkyl polyglycoside (c), allowing for significant improvements with respect to color lift, chromaticity and/or color intensity as compared to the use of conventional anionic, cationic or amphoteric surfactants. It is thus possible to provide surfactant-containing colorants whose color lift is comparable to that of aqueous colorants.

The agent can comprise a comparatively high fraction of amphoteric surfactants (b) and alkyl polyglycosides (c). These also act as emulsifiers for the dyes, so that their solubility is increased, so that the content of organic solvents in the colorant can be kept comparatively low.

EXAMPLES

The formulations summarized in Table 1 were prepared. Unless otherwise indicated, the quantity specifications are in each case percent by weight, based on the total weight. The specifications refer to the active substance content.

TABLE 1

Composition of the investigated comparative formulations V1, V2 and V3, and the formulations E1 and E1 as contemplated herein

| Formulation | V1 | V2 | V3 | E1 | E2 |
|---|---|---|---|---|---|
| Water | 99.70 | 94.70 | 94.45 | 93.55 | 91.92 |
| Sodium laureth-2-sulfate | | 5 | | | |
| Cocamidopropyl betaine | | | 5 | 3 | 1.52 |
| Lauryl polyglycoside (ex Plantacare ®) | | | | 3 | 6.18 |
| Direct-acting dye (see below) | 0.30 | 0.30 | 0.30 | 0.30 | 0.30 |
| NaCl | — | — | 0.25 | 0.15 | 0.08 |
| pH | [4.3-5.0] | [4.3-5.0] | [4.3-5.0] | [4.3-5.0] | [4.3-5.0] |

The direct-acting dyes summarized in Table 2 were used as direct-acting dyes.

TABLE 2

Direct-acting dyes used

| Name of the dye | Abbreviation used below |
|---|---|
| HC Blue 16 | A |
| Basic Violet 2 | B |
| Basic Yellow 57 | C |
| 4-hydroxypropylamino-3-nitrophenol | D |
| HC Red 13 | E |
| 4-amino-3-nitrophenol | F |

Color Lift, Color Intensity and Chromaticity

Before the staining process, hair strands (Kerling 10-0) were measured colorimetrically (Spectralflash SF 450 colorimetric device from Datacolor). Subsequently, the ready-to-use dyeing formulations prepared as described above were applied to the hair strands and left there at 20° C. for 30 minutes. The hair strands were then rinsed thoroughly and dried in the stream of air. After dyeing and drying, the hair strands were again measured colorimetrically. According to the following formula, the color distance ($\Delta E$) between undyed and dyed strand or the strand dyed with aqueous solution of the dye and the strand dyed with surfactant-containing colorant was calculated:

$$\Delta E = \sqrt{(Lv-Ln)^2+(av-an)^2+(bv-bn)^2}, \text{ with}$$

Lv, av, by colorimetry values before dyeing,

L n, an, bn colorimetry values after dyeing.

Similarly, the color distance ($\Delta E$) between the strand dyed with aqueous solution of the dye and the strand dyed with surfactant-containing colorant is calculated:

$$\Delta E = \sqrt{(Lw-Lt)^2+(aw-at)^2+(bw-bt)^2}, \text{ with}$$

Lw, aw, bw after dyeing with aqueous solution,

Lt, at, bt after dyeing with surfactant-containing colorant.

The chromaticity (chroma c, color direction) is calculated from the parameters a (CIE) and b (CIE) according to the following formula:

$$c = \sqrt{a^2+b^2}.$$

The measured and calculated data are summarized in Table 3.

TABLE 3

Results of the colorimetric investigations on the comparative formulations V1, V2 and V3, and the formulations E1 and E2 as contemplated herein

| Dye | Formulation | L (CIE) | a (CIE) | b (CIE) | Chroma c | ΔE (vs. Kerling 10-0) | ΔE (vs. aqueous colorant) |
|---|---|---|---|---|---|---|---|
| A | V1 | | | | 33.02 | 75.68 | |
| A | V2 | 68.35 | −4.63 | 7.97 | 9.21 | 15.41 | 62.70 |
| A | V3 | 26.59 | 6.83 | −34.91 | 35.58 | 74.47 | 7.05 |
| A | E1 | 23.97 | 9.84 | −35.07 | 36.43 | 76.69 | 4.41 |
| A | E2 | 32.04 | 1.69 | −35.19 | 35.24 | 70.82 | 14.08 |
| B | V1 | | | | 34.33 | 65.98 | |
| B | V2 | 47.66 | 41.49 | −11.86 | 43.15 | 59.17 | 25.95 |
| B | V3 | 25.96 | 38.60 | −4.18 | 38.82 | 68.03 | 4.97 |
| B | E1 | 27.28 | 45.38 | −9.92 | 46.46 | 73.15 | 13.85 |
| B | E2 | 25.90 | 37.94 | −3.27 | 38.08 | 67.40 | 4.04 |
| C | V1 | | | | 71.16 | 53.31 | |
| C | V2 | 75.59 | 1.71 | 22.96 | 23.03 | 4.49 | 49.00 |
| C | V3 | 70.82 | 6.25 | 62.01 | 62.33 | 43.85 | 11.23 |
| C | E1 | 70.58 | 8.15 | 66.93 | 67.43 | 48.96 | 6.87 |
| C | E2 | 71.94 | 7.46 | 63.72 | 64.16 | 45.53 | 9.68 |
| D | V1 | | | | 52.65 | 58.1 | |
| D | V2 | 43.53 | 44.86 | 28.26 | 53.02 | 56.40 | 3.19 |
| D | V3 | 44.64 | 44.25 | 27.84 | 52.28 | 55.18 | 4.30 |
| D | E1 | 44.41 | 44.65 | 27.90 | 52.65 | 55.65 | 4.06 |
| D | E2 | 45.07 | 45.59 | 27.72 | 53.36 | 55.98 | 4.85 |
| E | V1 | | | | 17.91 | 52.14 | |
| E | V2 | 47.40 | 15.72 | 3.28 | 16.06 | 37.15 | 15.79 |
| E | V3 | 38.91 | 17.51 | 0.98 | 17.54 | 45.81 | 6.89 |
| E | E1 | 38.43 | 18.19 | 0.53 | 18.19 | 46.64 | 6.36 |
| E | E2 | 45.75 | 16.85 | 0.14 | 16.85 | 40.32 | 13.70 |
| F | V1 | | | | 65.63 | 58.4 | |
| F | V2 | 56.01 | 34.60 | 51.18 | 61.78 | 51.36 | 8.66 |
| F | V3 | 53.34 | 40.08 | 54.91 | 67.98 | 58.43 | 4.92 |
| F | E1 | 57.77 | 34.46 | 52.21 | 62.56 | 51.22 | 10.10 |
| F | E2 | 54.56 | 40.71 | 56.14 | 69.35 | 59.13 | 6.62 |

The larger the color distance ΔE (vs. Kerling 10-0) between undyed strand and dyed strand, the stronger is the color lift resulting from the coloring. When applying the formulations E1 and E2, in each case compared to the comparative formulations V1 to V3, an above-average intensive color result was obtained for all the dyes investigated. In particular, the formulation E1 achieves particularly good results, which are not exceeded by the surfactant-containing formulations investigated for the dyes A, B, C, D and E. Better values are only achieved for dye F with the formulation E2.

The greatest possible chromaticity (that is, the highest possible value for chroma c) indicates a high color intensity. As can be seen from the calculated values from Table 3, when the formulations E1 and E2 are used, the highest chroma c values are obtained for all of the dyes investigated, compared to the comparative formulations V1 to V3, respectively. Again, the combination of the dye F with the formulation E2 proves to be particularly advantageous, while for the other dyes, better values are achieved with the formulation E1.

The parameter ΔE (vs. aqueous colorant) describes the color fidelity of the coloring from surfactant-containing solution with respect to coloring with an aqueous solution alone. Small values show a color lift of surfactant-containing solution which is similar to that of aqueous solution. Compared to the color lift from aqueous solution, the formulations E1 and E2 achieve predominantly good to very good values.

The measured value L (CIE) is a measure of the brightness or intensity of a coloring. Small measured values stand for a high intensity. The lower the L value, the greater the intensity of the coloring. In comparison to the formulations V1 to V3, good to very good L values could be measured continuously for the formulations E1 and E2. In particular, for the dyes A, C, D and E, a low L value could be achieved with the formulation E1, while for the dyes B and F, better values could be achieved with the formulation E2.

Overall, the formulations E1 and E2 as contemplated herein have above-average properties good with respect to the color lift, the color intensity and the chromaticity in comparison to conventional formulations.

The following formulations can be mentioned as further examples: (Amounts in % by weight, specifications "tel quel")

| Formulation | E3 | E4 | E5 | E6 |
|---|---|---|---|---|
| Water | 75.43 | 75.55 | 75.63 | 75.75 |
| Direct-acting dye | 0.50$^a$ | 0.38$^b$ | 0.30$^c$ | 0.18$^d$ |
| Cocamidopropyl betaine (37% by weight active content) | 4.00 | 4.00 | 4.00 | 4.00 |
| Lauryl polyglucoside (51% by weight active content) | 12.00 | 12.00 | 12.00 | 12.00 |
| Associative thickener (cetylhydroxyethylcellulose, Natrosol ™ Plus 33 CS) | 1.40 | 1.40 | 1.40 | 1.40 |
| Film former (Polyquaternium-37 or Polyquaternium-10) | 0.60 | 0.60 | 0.60 | 0.60 |
| 1,2-propanediol | 3.00 | 3.00 | 3.00 | 3.00 |
| Sodium benzoate | 0.40 | 0.40 | 0.40 | 0.40 |
| NaOH (50% by weight) | 0.02 | 0.02 | 0.02 | 0.02 |
| D-panthenol (75% by weight) | 0.20 | 0.20 | 0.20 | 0.20 |
| Perfume | 0.90 | 0.90 | 0.90 | 0.90 |
| Succinic acid | 0.20 | 0.20 | 0.20 | 0.20 |
| Trimagnesium citrate | 0.20 | 0.20 | 0.20 | 0.20 |
| Citric acid monohydrate | 0.40 | 0.40 | 0.40 | 0.40 |
| Castor oil (hydrogenated, 40 EO) | 0.50 | 0.50 | 0.50 | 0.50 |
| PEG-7 glyceryl cocoate | 0.25 | 0.25 | 0.25 | 0.25 |

$^a$ HC Red 3
$^b$ Dye mixture of N,N'-bis-(2-hydroxyethyl)--2-nitro-p-phenylenediamine and HC Blue 12
$^c$ Dye mixture of HC Red 3 and HC Orange 1
$^d$ Dye mixture of HC Blue 12, HC Blue 16 (Blue Quat Bromide), HC Yellow 2, N,N'-bis-(2-hydroxyethyl)--2-nitro-p-phenylenediamine, Ext. D&C Violet 2, Basic Brown 17, Basic Red 76, and Basic Yellow 57

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing of keratinic fibers, comprising, in a cosmetic carrier
   (a) at least one direct-acting dye,
   (b) cocamidopropyl betaine, and
   (c) lauryl glucoside,
   wherein the total amount of (b) in the agent, based on the weight of the agent, is less than the total amount of (c) or equal to the total amount of (c).

2. The agent according to claim 1, wherein the total content of (b) and (c) together is from about 1.0 to about 25.0% by weight, based on the total weight of the agent.

3. The agent according to claim 1, wherein (b) is present in a total amount of from about 0.5 to about 15.0% by weight, based on the weight of the agent.

4. The agent according to claim 1, wherein (c) is present in a total amount of from about 0.5 to about 15.0% by weight, based on the weight of the agent.

5. The agent according to claim 1, wherein the agent comprises from about 0 to about ≤0.2% by weight of surfactants which include a sulfate group.

6. The agent according to claim 1, wherein the agent comprises ≤0.2% by weight, based on the total weight of the agent, of anionic surfactants.

7. The agent according to claim 1, wherein the at least one direct-acting dye is present in a total amount from about 0.001 to about 7% by weight, based on the weight of the agent.

8. The agent according to claim 1, wherein the agent further comprises at least one associative thickener, in an amount, based on the total weight of the agent, of from about 0.1 to about 5% by weight.

9. The agent according to claim 1, wherein the agent further comprises at least one film former, in an amount, based on the total weight of the agent, of from about 0.1 to about 5% by weight.

10. The agent according to claim 1, wherein the agent comprises at least one non-ionic associative thickener and at least one cationic polymer, in combination with each other.

11. A method for coloring keratinic fibers, in which an agent according to claim 1 is applied to the keratinic fibers.

12. The agent according to claim 1, comprising
the at least one direct-acting dye (a) in a total amount from about 0.6 to about 1% by weight, based on the weight of the agent;
the cocamidopropyl betaine (b) in a total amount of from about 1.3 to about 4.0% by weight, based on the weight of the agent;
the lauryl glucoside (c) in a total amount of from about 6.0 to about 8.0% by weight, based on the weight of the agent.

13. The agent according to claim 1, wherein the dye comprises HC Blue 16.

14. The agent according to claim 1, wherein the dye comprises Basic Violet 2.

15. The agent according to claim 1, wherein the dye comprises Basic Yellow 57.

16. The agent according to claim 1, wherein the dye comprises 4-hydroxypropylamino-3-nitrophenol.

17. The agent according to claim 1, wherein the dye comprises HC Red 13.

18. The agent according to claim 1, wherein the dye comprises 4-amino-3-nitrophenol.

\* \* \* \* \*